United States Patent
Bastide et al.

(10) Patent No.: US 10,586,615 B2
(45) Date of Patent: Mar. 10, 2020

(54) ELECTRONIC HEALTH RECORD QUALITY ENHANCEMENT

(71) Applicant: International Business Machines Corporation, Armonk, NY (US)

(72) Inventors: Paul R. Bastide, Boxford, MA (US); Matthew E. Broomhall, Goffstown, NH (US); Robert E. Loredo, North Miami Beach, FL (US)

(73) Assignee: International Business Machines Corporation, Armonk, NY (US)

( * ) Notice: Subject to any disclaimer, the term of this patent is extended or adjusted under 35 U.S.C. 154(b) by 676 days.

(21) Appl. No.: 15/340,314

(22) Filed: Nov. 1, 2016

(65) Prior Publication Data

US 2018/0121607 A1     May 3, 2018

(51) Int. Cl.
   *G16H 10/60*     (2018.01)
   *G16H 10/20*     (2018.01)

(52) U.S. Cl.
   CPC .............. *G16H 10/60* (2018.01); *G16H 10/20* (2018.01)

(58) Field of Classification Search
   CPC .................................................... G16H 10/60
   See application file for complete search history.

(56) References Cited

U.S. PATENT DOCUMENTS

| | | | |
|---|---|---|---|
| 7,353,238 B1* | 4/2008 | Gliklich | ........... G06Q 10/06375 |
| 7,428,494 B2 | 9/2008 | Hasan | |
| 8,428,966 B2 | 4/2013 | Green et al. | |
| 8,612,254 B2 | 12/2013 | Warner et al. | |
| 8,762,169 B2 | 6/2014 | Mohlenbrock et al. | |
| 2003/0149597 A1* | 8/2003 | Zaleski | ............... G06F 19/3481 705/2 |
| 2005/0177403 A1* | 8/2005 | Johnson | ................. G06Q 10/00 705/20 |
| 2009/0271218 A1* | 10/2009 | Mok | ..................... G06F 19/325 705/3 |
| 2011/0295618 A1 | 12/2011 | Naipaul | |
| 2012/0310661 A1* | 12/2012 | Greene | ................ G06Q 10/087 705/2 |
| 2013/0275149 A1 | 10/2013 | Gaines et al. | |
| 2013/0325509 A1 | 12/2013 | McCarrick | |
| 2013/0339053 A1 | 12/2013 | Jacobs et al. | |
| 2014/0214444 A1 | 7/2014 | Thesman | |
| 2014/0236630 A1 | 8/2014 | Murata | |

(Continued)

OTHER PUBLICATIONS

Khan et al.; "Personalized Electronic Health Record System for Monitoring Patients With Chronic Disease", SIEDS IEEE International Conference on, Apr. 26, 2013, pp. 121-126.

(Continued)

*Primary Examiner* — John A Pauls
(74) *Attorney, Agent, or Firm* — Ryan Lewis; Edell, Shapiro & Finnan, LLC

(57) ABSTRACT

A method of managing electronic health records comprises identifying an update by a healthcare provider to an electronic health record of a patient and evaluating a quality of the identified update. In response to the identified update failing the quality evaluation, a survey including at least one inquiry is generated and transmitted to one or more selected from a group of the healthcare provider and the patient. Information within the electronic health record may be modified based on one more responses to the at least one inquiry of the survey.

17 Claims, 4 Drawing Sheets

(56) References Cited

U.S. PATENT DOCUMENTS

| | | |
|---|---|---|
| 2014/0278550 A1 | 9/2014 | Pestka |
| 2015/0066536 A1 | 3/2015 | Spates |
| 2015/0317436 A1 | 11/2015 | Kutty |
| 2015/0356270 A1 | 12/2015 | Devarakonda et al. |
| 2016/0042431 A1 | 2/2016 | Douglass et al. |
| 2016/0093010 A1 | 3/2016 | Vasiliu-Feltes et al. |

OTHER PUBLICATIONS ip.com et al.; "Clinical Content Categorization from Electronic Medical Records (EMRs) without Assignment of Codes", IPCOM000245141D, Feb. 12, 2016, pp. 1-15.

OpenMRS, http://openmrs.org/, retrieved from Internet Jan. 8, 2016, 5 pages.

Epic, http://www.epic.com/, Epic Systems Corporation, 2016, 1 page.

Electronic Health Records, http://www.practicefusion.com/, Practice Fusion, Inc., 2016, 8 pages.

Cerner, http://clinfowiki.org/wiki/index.php/Cerner#Millennium_Objects, Clinfowiki, Sep. 2015, 10 pages.

* cited by examiner

ELECTRONIC HEALTH RECORD QUALITY ENHANCEMENT

BACKGROUND

1. Technical Field

Present invention embodiments relate to computer systems and methods for managing electronic health records and, more particularly, computer systems and methods for enhancing the quality of electronic health records being managed.

2. Discussion of the Related Art

An electronic health record (EHR) is an electronic version of a patient's medical history, that is maintained by the provider over time, and may include all of the key administrative clinical data relevant to that persons care under a particular provider, including demographics, progress notes, problems, medications, vital signs, past medical history, immunizations, laboratory data and radiology reports The EHR automates access to information and has the potential to streamline the clinician's workflow. The EHR also has the ability to support other care-related activities directly or indirectly through various interfaces, including evidence-based decision support, quality management, and outcomes reporting.

With EHR records, there is a variance in the quality of the updates to the EHR records. One doctor uses an abbreviated recording style, another uses a detailed style, and yet another enters the bare minimum to save the form.

There is a need for consistent high quality interaction with EHR records.

SUMMARY

According to an example embodiment of the present invention, a method of managing electronic health records comprises identifying an update by a healthcare provider to an electronic health record of a patient; evaluating a quality of the identified update; in response to the update failing the quality evaluation, generating and transmitting a survey including at least one inquiry to one or more selected from a group of the healthcare provider and the patient; and modifying information within the electronic health record based on one more responses to the at least one inquiry of the survey.

According to another example embodiment of the present invention, a system for managing electronic health records comprises at least one processor configured to: identify an update by a healthcare provider to an electronic health record of a patient; evaluate a quality of the identified update; in response to the identified update failing the quality evaluation, generate and transmit a survey including at least one inquiry to one or more selected from a group of the healthcare provider and the patient; and modify information within the electronic health record based on one more responses to the at least one inquiry of the survey.

According to yet another example embodiment of the present invention, a computer program product for managing electronic health records comprises a computer readable storage medium having program instructions embodied therewith, the program instructions executable by a computer processor to cause the computer processor to: identify an update by a healthcare provider to an electronic health record of a patient; evaluate a quality of the identified update; in response to the identified update failing the evaluation, generate and transmit a survey including at least one inquiry to one or more selected from a group of the healthcare provider and the patient; and modify information within the electronic health record based on one more responses to the at least one inquiry of the survey.

BRIEF DESCRIPTION OF THE DRAWINGS

Generally, like reference numerals in the various figures are utilized to designate like components.

DETAILED DESCRIPTION

Figure 1:
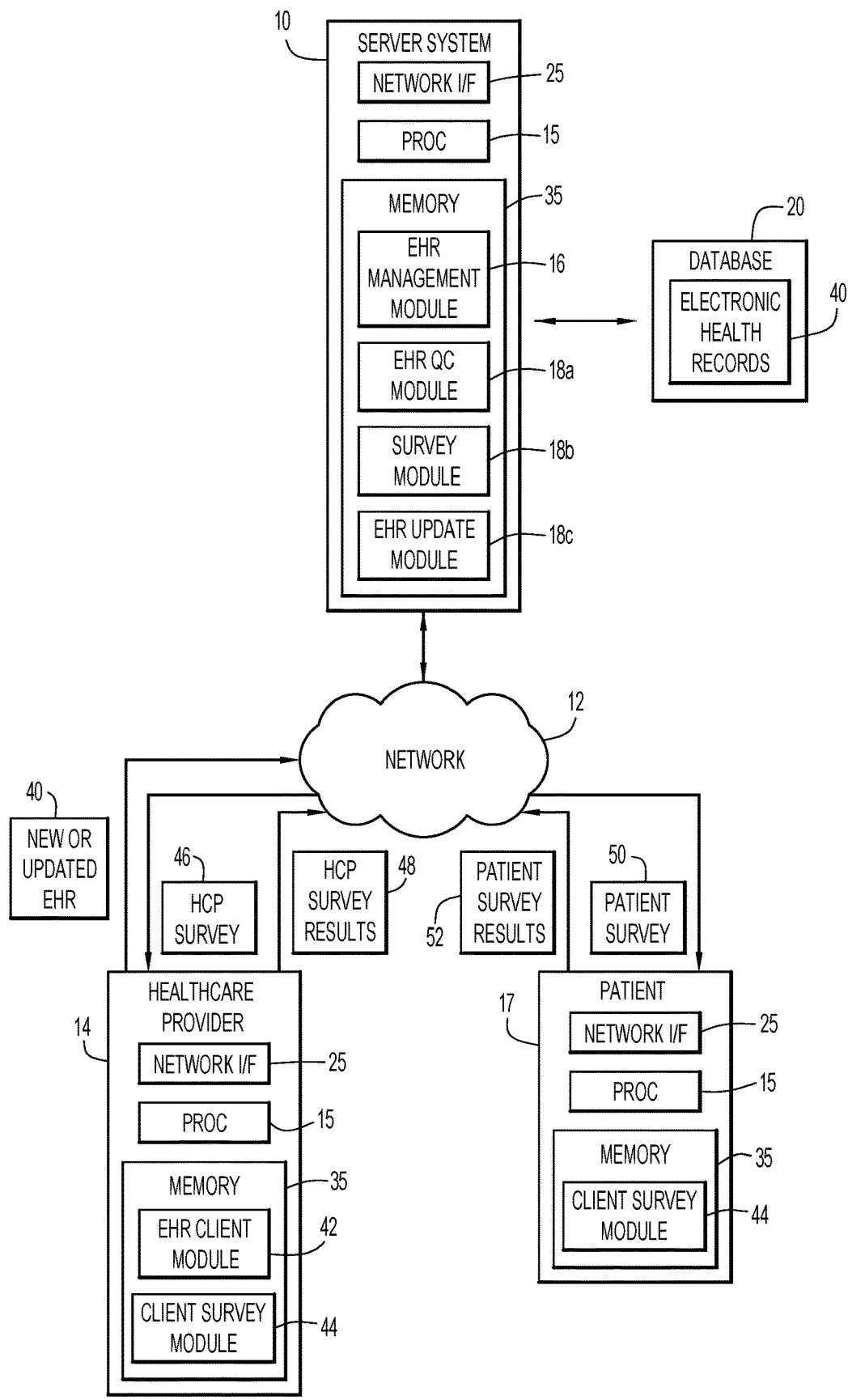
FIG. 1 is a diagrammatic illustration of an example computing environment implementing an embodiment of the present invention.

Electronic health records (EHRs) may include free-form fields that allow a healthcare provider to enter information about a patient as unstructured text. When an EHR is updated (e.g., created or modified), the quality of the update may vary considerably from one healthcare provider to another healthcare provider based at least in part on the information entered by the health provider in one or more free-form fields. For example, one healthcare provider may provide only the bare minimum amount of information required to save the form, while another healthcare provider may enter very comprehensive and detailed information.

Present invention embodiments assess the quality of an update to a free-form field in an EHR and, if the quality of the update is determined to be unsatisfactory, initiate processes to enhance the quality of the EHR (e.g., by generating one or more surveys and modifying information in the EHR based on the results of the one or more surveys). Present invention embodiments may assess the most recent updates from a given patient-provider session, or all updates over a specified period of time (e.g., the past year, or the entire patient history). Quality of an EHR update may be assessed using a model, such as a classifier, that determines whether the update is satisfactory or unsatisfactory. The model may assign a metric or score indicating a probability that the update is satisfactory or unsatisfactory.

Present invention embodiments may assess updates to any free-form field in an EHR, including but not limited to free-form fields such as Patient Visit Information or Observation Record or Z Segments as specified by Health Level Seven ("HL7"), a set of international standards for transfer of clinical and administrative data between software applications used by healthcare providers. Present invention embodiments may assess all of the free-form fields in an EHR, or the assessment may be limited to a subset of the total number of free-form fields. In an example embodiment, the subset may include only those fields associated with a specific disease or illness where there is a higher risk for the outcome. In another example embodiment, the subset may include only those fields associated with one or more specific types of messages (e.g., ORU or ADT messages in an EHR system using HL7 messaging standards).

Examples of factors that may be used by present invention embodiments to assess the quality of an update include:

Natural Language/Readability—the quality of the writing, the grammar, the length of the update;

Medical Terminology—the form of the update, detecting copied EHR content;

Form/Record—Evaluate the required and the optional fields against the average filled-in;

Patient Satisfaction/Outcome—Retrieving the prior patient satisfaction or the person's prior happiness, or happiness upon leaving the appointment;

Usefulness of the Data—The usefulness of the data in future analytics;

Disparities with common accepted update practices; and/or

Patient geographic changes.

Rather than focusing solely on patient outcomes, present invention embodiments may take into account other factors, such as readability of notes for one skilled in a medical area/field related to the free form text/field. In an example embodiment, readability may be determined using natural language processing to analyze a corpus of selected doctors notes from a specific field for Parts-of-Speech, Terms, Grammar, N-Grams, length, etc.

In present invention embodiments, each of the selected notes may be converted into a vector matched with success. Anti-patterns (commonly recurring patterns associated with failure) for doctor notes may be included if they are over a minimum length. Present invention embodiments may use such information to generate a success/failure model, which may be a simple classifier or a more complex model. In an example embodiment, doctors may be limited from selecting their own notes for analysis and generation of the model. In another example embodiment, the selection may be done based on a general consensus for a field.

Present invention embodiments may assign a value to each update to a free-form field of an EHR, retrieve a quality threshold, and compare the value assigned to the update against the quality threshold. In example embodiments, if the value assigned to the update equals or exceeds the quality threshold, the update may be deemed satisfactory and no further action taken. On the other hand, if the value assigned to the update is lower than the quality threshold, present invention embodiments may initiate a process to enhance the EHR, for example by generating a survey. In example embodiments, the quality threshold may be doctor-specific, practice-specific, or institution-specific. In the event of multiple updates, present invention embodiments may provide a total calculated quality by summing values and may compare the threshold against the total calculated quality.

Present invention embodiments may generate a provider survey, a patient survey, or both types of surveys. In exemplary embodiments, the surveys may include a biometric sampling or questions generated to fill gaps in the EHR. The biometric survey may automatically be initiated after detection of low quality. The survey may require a patient's agreement.

In example embodiments, the questions may be selected from a set of preapproved questions. In example embodiments, the set of preapproved questions may be related to a specific detected malady of the patient. In example embodiments, the set of preapproved questions may be stored in memory for retrieval. In example embodiments, the survey may be generated by the provider or the survey may be generated dynamically using natural language generation (NLG). In exemplary embodiments, the prediction of a poor update may prompt surveying prior to the actual update—for instance if prior data suggests that a particular doctor spends minimal time updating.

Present invention embodiments may be used to determine agreement between the provider and patient based on dual surveys. For example, if the result of the two surveys generates an unexpected result, or they differ in some way, present invention embodiments may alert the provider and/or the patient to take an action to resolve the missed expectation.

Present invention embodiments may initiate a process to enhance an EHR in the event of an inadequate update. For example, present invention embodiments may modify the update by augmenting the EHR with provider survey results and/or patient survey results. In example embodiments, the survey results may be forwarded electronically to other entities for secondary review.

Present invention embodiments may also be used to evaluate a provider's record keeping, and/or to perform subsequent analysis of an augmented EHR record.

For example, in a first scenario, Doctor Alice is registered as a doctor in an EHR system, and Bob is entered as a patient in the EHR system. Bob meets with Doctor Alice with regards to a malady. Doctor Alice updates Bob's EHR to include the following unstructured text:

XYZ, AD, PM iii of ABC solution where XYZ=malady, AD=right ear, PM=evening, iii=three times a day, and ABC is the name of a medication.

Present invention embodiments analyze the update and determine that the quality is 50, which is below a predefined quality threshold of 100. To enhance the quality of the EHR, a survey is generated for the patient. For example, the survey may ask the patient the following questions:

1. Is the three times daily of ABC helping you?
2. What malady best describes how you feel right now?

The patient, Bob, receives the survey and enters responses to the questions above. For example, Bob may answer "I am taking the medicine three times a day; it's OK" to the first question and "nauseated" to the second question. Bob may then submit the completed survey.

Present invention embodiments may receive the completed survey and augment the EHR with the data to generate higher quality. Present invention embodiments may replace the prior update in the EHR, or add an additional message that updates the EHR.

Alternatively, or in addition to sending a survey to the patient, present invention embodiments may send a survey to the healthcare provider. For example, after determining that the quality of the above update is below the quality threshold, present invention embodiments may send a survey to Doctor Alice asking the doctor for blood pressure data to confirm the malady. Doctor Alice may also be asked to answer the following question about Bob's condition:

What malady best describes how the patient feels right now?

After Doctor Alice completes the survey (e.g., by providing the requested blood pressure data and noting the malady described by the patient), present invention embodiments may augment the update to the EHR with the survey data to generate higher quality.

An example environment for use with present invention embodiments is illustrated in FIG. 1. Specifically, the environment includes one or more server systems 10, one or more first client systems 14, and one or more second client systems 17. Server systems 10 and client systems 14, 17 may be remote from each other and communicate over a network 12. The network 12 may be implemented by any number of any suitable communications media (e.g., wide area network (WAN), local area network (LAN), Internet, Intranet, etc.). Alternatively, server systems 10 and at least some of the client systems 14, 17 may be local to each other, and communicate via any appropriate local communication medium (e.g., local area network (LAN), hardwire, wireless link, Intranet, etc.).

In an example embodiment, server systems 10 may include an EHR management module 16 to facilitate creation, modification, storage, and retrieval of EHRs by healthcare providers and other healthcare personnel (e.g., healthcare administrators, information technology professionals, etc.). Present invention embodiments may be embedded into and/or coupled with current EHR systems, such as Cerner, Epic, etc., as well as future EHR systems.

Server systems 10 may also include an EHR quality assessment module 18a for evaluating the quality of EHRs (e.g., a new or updated EHR 40) managed by the system, a survey module 18b for generating surveys (e.g., surveys 46 & 50) that may be communicated to a healthcare provider and/or a patient, and an EHR update module 18c for making changes to the EHR based on survey results (e.g., survey results 48 and 52). Modules 16, 18a, 18b, and 18c may be combined into a single module. Alternatively, modules 16, 18a, 18b, and 18c may be separate as shown, and it will be appreciated that one of more of the modules may each include one or more modules or units to perform the various functions of present invention embodiments described below. The various modules (e.g., modules 16 and 18a-c) may be implemented by any combination of any quantity of software and/or hardware modules or units, and may reside within memory 35 of the server for execution by processor 15.

A database system 20 may store EHRs 40 and various other types of information (e.g., training data for building a quality evaluation model). The database system 20 may be implemented by any conventional or other database or storage unit, may be local to or remote from server systems 10, and may communicate via any appropriate communication medium (e.g., local area network (LAN), wide area network (WAN), Internet, hardwire, wireless link, Intranet, etc.).

Client systems 14 may be configured to enable a healthcare provider to create new EHRs and update existing EHRs by use of an EHR client module 42 running on client 14. Client systems 14 may also be configured to receive and complete surveys generated by the server systems 10 by use of a client survey module 44. Modules 42 and 44 may be combined into a single module. Alternatively, modules 42 and 44 may be separate as shown, and it will be appreciated that one of more of the modules may each include one or more modules or units to perform the various functions of present invention embodiments described below. The various modules of client systems 14 (e.g., modules 42 and 44) may be implemented by any combination of any quantity of software and/or hardware modules or units, and may reside within memory 35 of the client systems 14 for execution by processor 15 of the client systems 14. Alternatively, a client system 14 may be a thin client, and one or more of the modules 42 and 44 may reside within memory 35 of the server systems 10 for execution by processor 15 of the server systems when accessed by client system 14.

Client systems 17 may be configured to enable patients to receive and complete surveys generated by the server systems 10 by use of a client survey module 44. Module 44 of client systems 17 may include one or more modules or units to perform the various functions of present invention embodiments described below. Module 44 of client systems 17 may be implemented by any combination of any quantity of software and/or hardware modules or units, and may reside within memory 35 of the client systems 17 for execution by processor 15 of the client systems 17. In an alternative example, a client system 17 may be a thin client, and module 44 may reside within memory 35 of the server systems 10 for execution by processor 15 of the server systems when accessed by client system 17.

Alternatively, server systems 10 may be configured to send electronic communications (e.g., via email) regarding surveys to clients 14 and/or clients 17 using survey module 18b. Such communications may include a survey (e.g., a healthcare provider survey 46 or a patient survey 50) or they may include a request prompting the healthcare provider or patient to complete a survey by accessing a client survey module 44 on the client system or a survey module 18b on server system 10. Healthcare provider clients 14 may be configured to return survey results 48 via electronic communications with survey module 18b of server systems 10, e.g., by entering responses directly into survey module 18b, or by using a client survey module 44 on client system 14 to enter responses, or by emailing the responses. Similarly, patient clients 17 may be configured to return survey results 52 via electronic communications with survey module 18b of server systems 10, e.g., by entering responses directly into survey module 18b, or by using a client survey module 44 on client system 17 to enter responses, or by emailing the responses.

The client systems 14, 17 may present a graphical user interface (e.g., GUI, etc.) or other interface (e.g., command line prompts, menu screens, etc.) to display EHRs (e.g., in the case of client systems 14) and/or surveys and to accept input from users (e.g., updates to the EHRs, survey responses, etc.).

Server systems 10 and client systems 14, 17 may be implemented by any conventional or other computer systems preferably equipped with a display or monitor, a base (e.g., including at least one processor 15, one or more memories 35 and/or internal or external network interfaces or communications devices 25 (e.g., modem, network cards, etc.)), optional input devices (e.g., a keyboard, mouse or other input device), and any commercially available and custom software (e.g., server/communications software, modeling module, analysis module, modules 16 and 18, browser/interface software, etc.).

Figure 2:
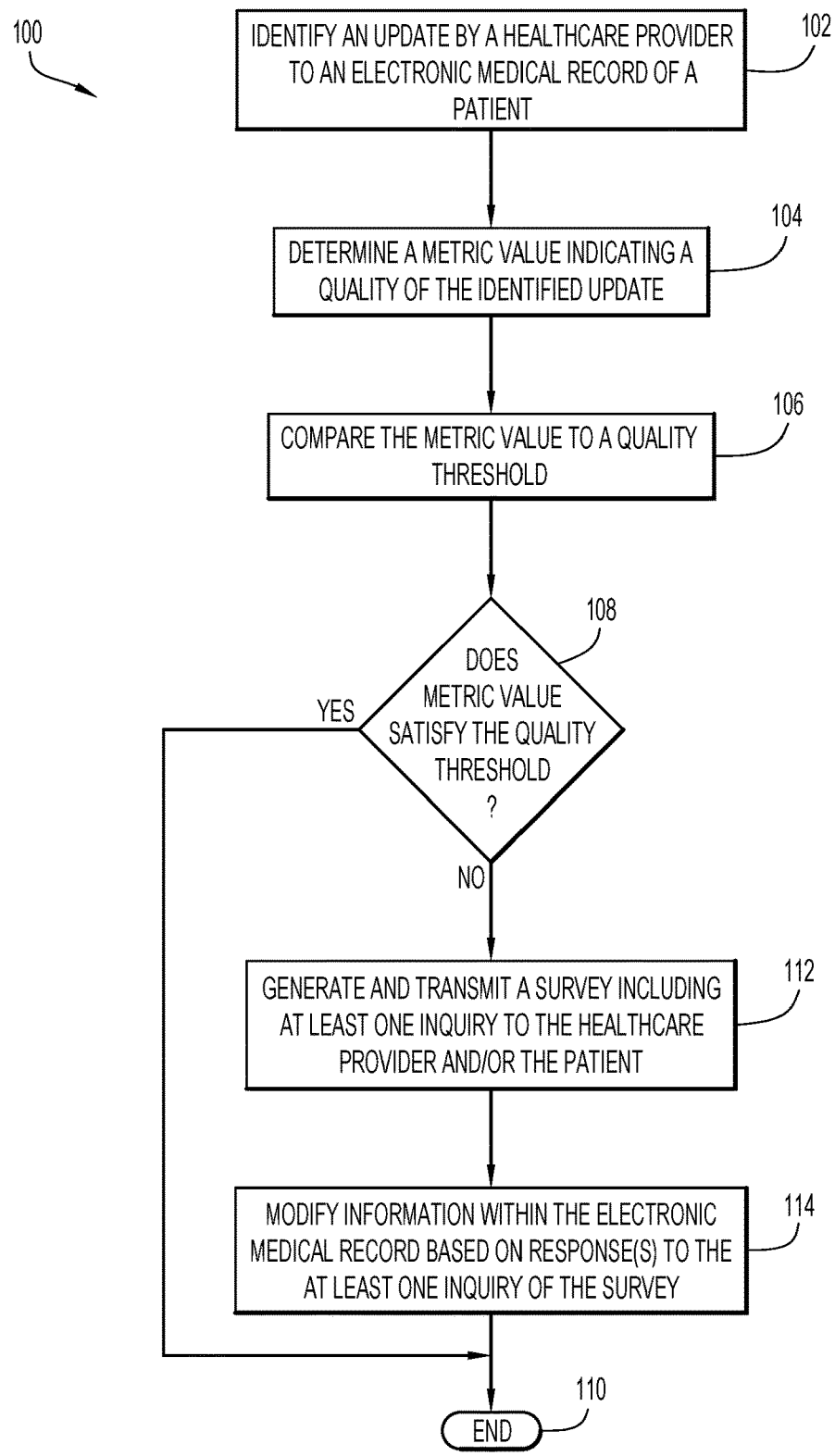
FIG. 2 is a procedural flowchart illustrating a manner of assessing the quality of an EHR and enhancing the quality of the EHR according to an embodiment of the present invention.

A manner of evaluating and enhancing EHR quality according to an example embodiment is illustrated in FIG. 2 at 100. Initially, an update to an EHR is identified at step 102 (e.g., via EHR management module 16 and at least one server system 10). For example, server 10 may be configured to monitor messages between EHR client modules 42 on clients 14 and EHR management module 16 on server 10 and to identify messages making an update to an EHR (e.g., creating a new EHR or modifying an existing EHR). In example embodiments, the server 10 may be configured to identify an update to an unstructured data (e.g., a free form text field) in an EHR.

If an update to an EHR is identified in step 102, a metric value indicating a quality of the identified update may be determined in step 104 (e.g., via EHR QC module 18a and at least one server system 10). In example embodiments, a metric value indicating a quality of an update to an EHR may be based on a number of factors, such as patient satisfaction/outcome, readability of the notes, medical terminology, usefulness of the data in future analytics, disparities with common accepted update practices, and/or patient geographic changes. For example, natural language processing may be used to analyze the identified update for Parts-of-Speech, Terms, Grammar, N-Grams, length, etc., and a quality metric value may be determined by comparing the results of the natural language processing of the update with results from natural language processing of a corpus of selected doctors notes of known quality from a specific field. For example, a corpus of selected doctors notes having pre-determined quality values may be analyzed using natural language processing, and a quality metric value for the update may be determined by matching the update to selected doctors notes of similar readability. In example embodiments, a plurality of the foregoing factors may be used to determine a quality metric value, e.g., by summing quality metric values for each factor. In example embodiments, factors determining quality may be assigned different weights and an overall quality metric value of an update may be a weighted sum of quality metric values.

In step 106, the metric value determined in step 104 may be compared against a pre-determined quality threshold (e.g., via EHR QC module 18a and at least one server system 10). For example, the quality threshold may be a number selected based on an analysis of the corpus of doctors notes and the factors outlined above. In example embodiments, the quality threshold may be adjusted based on changes to the corpus of selected doctors notes or user preference.

In step 108, a determination is made whether or not the metric value determined in step 104 satisfies the quality threshold (e.g., via EHR QC module 18a and at least one server system 10). For example, the metric value may be determined to satisfy the quality threshold if it is equal to or greater than the quality threshold. If the metric value is determined to satisfy the quality threshold, then the quality assessment process may end at step 110 and the update may be saved to the EHR database without substantive modification.

If the metric value is determined not to satisfy the quality threshold, a computer process may be initiated to enhance the quality of the update. For example, in step 112, an electronic survey including at least one inquiry may be generated and transmitted to the healthcare provider and/or the patient (e.g., via survey module 18b and at least one server 10). In example embodiments, predetermined surveys for a plurality of maladies or ailments may be stored in a database, and generating the survey may include selecting a survey from the plurality of predetermined surveys based on malady or ailment. In other example embodiments, the survey may be generated based on data in the corpus of doctors notes stored in a database (e.g., seeking information that appears in doctors notes deemed successful). The survey may include free form and/or structured inquiries.

In step 114, once response(s) to the at least one inquiry of the survey are received, the update may be enhanced by modifying information within the EHR based on the response(s) (e.g., via EHR update module 18c and at least one server 10). At step 110, the quality assessment and enhancement process may end, and the modified EHR may be saved to the EHR database. In an optional embodiment, steps 104, 106, 108, 112 and 114 may be repeated for the modified EHR to ensure that the enhanced version satisfies the quality threshold.

Figure 3:
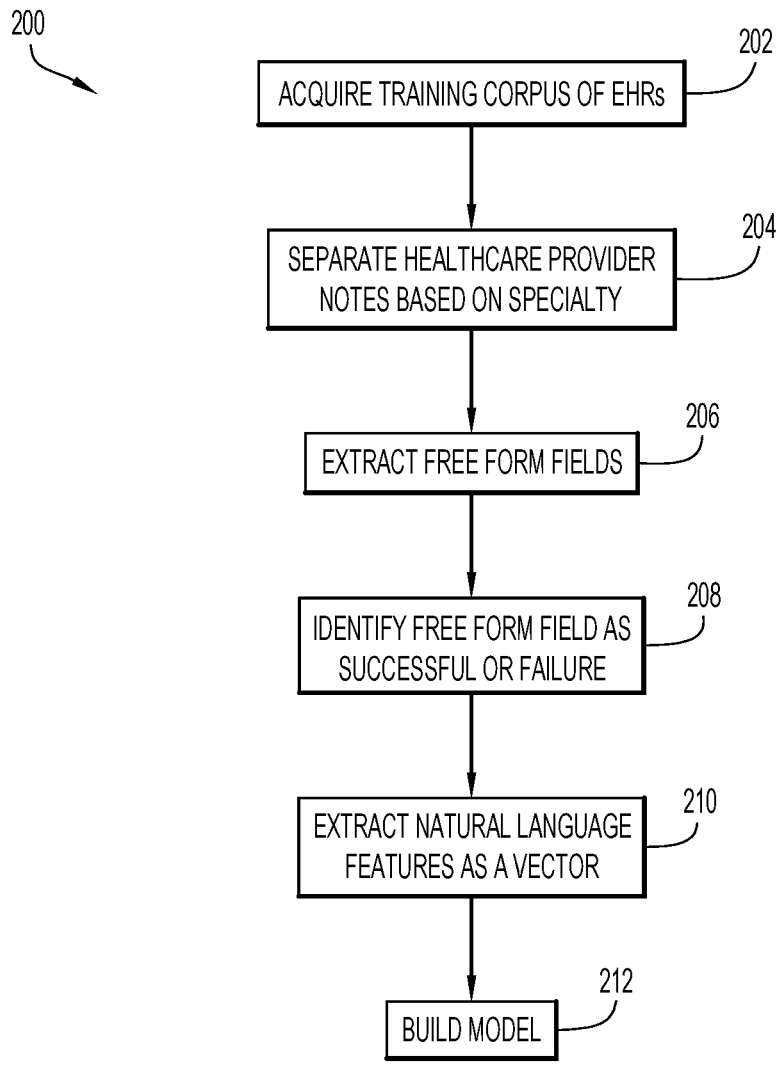
FIG. 3 is a procedural flowchart illustrating a manner of building a statistical model for assessing the quality of an entry in an EHR according to an embodiment of the present invention.

A manner of building a model to assess the quality of an update to an EHR according to an example embodiment is illustrated in FIG. 3 at 200. In example embodiments, the steps shown in FIG. 3 may be performed by EHR QC module 18a and at least one server 10. Initially, a corpus of EHRs with free form text fields is acquired in step 202. For example, the corpus may include the EHRs in database 20.

In step 204, healthcare provider notes in the EHRs are separated based on specialty (e.g., via EHR QC module 18a and at least one server 10). For example, the corpus of EHRs may be classified into a plurality of groups according to healthcare specialty, such as internal medicine, orthopedics, neurology, urology, gynecology, gastroenterology, pediatrics, radiology, oncology, ophthalmology, etc.

In step 206, free form text fields are extracted from the EHRs in each specialty. In example embodiments, the extracted text fields may be stored in memory 35 or database 20.

In step 208, each of the extracted free form text fields is identified as either a success or a failure. The identification of an extracted free form text field as a success or a failure may be based on patient outcome.

In step 210, the extracted free form text fields are analyzed using natural language processing. For example, natural language features (e.g., Parts-of-Speech, Terms, Grammar, N-Grams, length, etc.) of the extracted free form text fields may be extracted as a vector.

In step 212, a model is built for determining whether a free form text field is a success or a failure using the vectors from step 210 and the determination in step 208 whether the associated free form text fields are a success or a failure. In one example, each of the vectors may be assigned a binary label of "success" or "failure." In another example, each of the vectors may be assigned a scaled label indicating a degree of success (e.g., 60% successful). Various types of models and machine learning techniques can be used. In an example embodiment, the model can be a simple classifier model.

Figure 4:
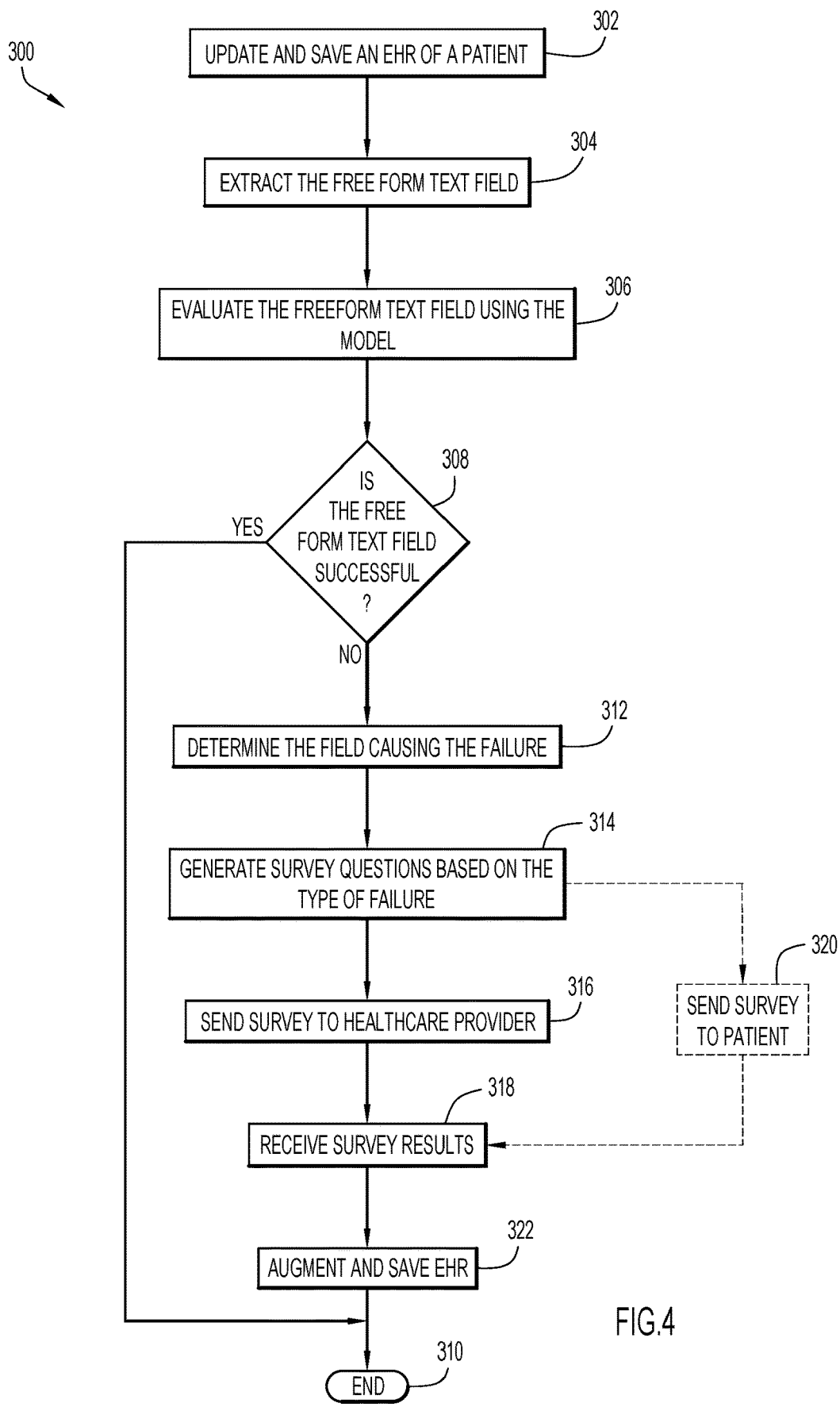
FIG. 4 is a procedural flowchart illustrating a manner of using a model to assess the quality of an EHR and enhancing the EHR according to an embodiment of the present invention.

A manner of evaluating and enhancing the quality of an EHR according to an example embodiment is illustrated in FIG. 4 at 300. Initially, an EHR of a patient is updated and saved at step 302 (e.g., via EHR management module 18a and at least one server system 10).

In step 304, an auditing process is initiated, causing a free form text field to extracted from the EHR (e.g., via EHR QC module 18a and at least one server system 10).

In step 306, the extracted free form text field is evaluated using a model (e.g., a classifier model residing in EHR QC module 18a and at least one server system 10).

In step 308, a determination is made whether or the extracted free form text field is a success or a failure using the model (e.g., via EHR QC module 18a and at least one server system 10). In one example embodiment, the determination may include matching attributes of the extracted free form text field to attributes of prior free form text fields of predetermined quality for the same specialty and making a binary determination of "success" or "failure." In another example embodiment, the determination may include assigning a quality metric value to the extracted free form text field and comparing the assigned quality metric value to a predetermined quality threshold.

If the extracted free form text field is determined to be successful, then the evaluation process may end at step 310.

If the extracted free form text field is determined to be a failure, then the field causing the failure may be determined in step 312 (e.g., via EHR QC module 18a and at least one server system 10).

In step 314, one or more survey questions (inquiries) based on the type of failure may be generated (e.g., via survey module 18b and at least one server system 10). In example embodiments, predetermined questions for a plurality of maladies or ailments may be stored in a database, and generating the questions may include selecting one or more questions from the plurality of predetermined questions based on malady or ailment. In other example embodiments, the questions may be generated based on data in the corpus of doctors notes stored in a database (e.g., seeking information that appears in doctors notes deemed successful). The one or more questions may include free form and/or structured inquiries.

In step 316, a survey containing the questions generated in step 314 may be sent to the healthcare provider (e.g., via survey module 18b and at least one server system 10).

In step 318, responses to the questions may be received from the heath care provider (e.g., via survey module 18b and at least one server system 10).

In addition to, or as an alternative to, the healthcare provider survey, a survey containing one or more questions generated in step 314 may be sent to the patient in optional step 320, and the patient's responses may be received in step 318.

In step 322, the EHR may be augmented based on the survey responses received from the healthcare provider and/or the patient (e.g., via EHR update module 18c and at least one server system 10). If survey responses are received from both the healthcare provider and the patient in step 322 (or in the process 100 illustrated in FIG. 2), responses to the survey from the healthcare provider and the patient may be compared, and the healthcare provider and/or the patient may be notified to perform an action in response to at least one difference between their respective responses. In another example embodiment, the one or more responses from the patient to the at least one inquiry of the survey may also be provided to the healthcare provider or another entity for review.

It will be appreciated that the embodiments described above and illustrated in the drawings represent only a few of the many ways of enhancing the quality of EHRs.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, modeling module, analysis module, etc.). These systems may include any types of monitors and input devices (e.g., keyboard, mouse, voice recognition, etc.) to enter and/or view information.

It is to be understood that the software (e.g., EHR management module, EHR quality evaluation module, survey module, EHR update module, modules 16 and 18a-c, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., EHR management module, EHR quality evaluation module, survey module, EHR update module, modules 16 and 18a-c, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., EHRs, training data, survey results, etc.). The database system may be implemented by any number of any conventional or other databases, data stores or storage structures (e.g., files, databases, data structures, data or other repositories, etc.) to store information (e.g., EHRs, training data, survey results, etc.). The database system may be included within or coupled to the server and/or client systems. The database systems and/or storage structures may be remote from or local to the computer or other processing systems, and may store any desired data (e.g., EHRs, training data, survey results, etc.).

The present invention embodiments may employ any number of any type of user interface (e.g., Graphical User Interface (GUI), command-line, prompt, etc.) for obtaining or providing information (e.g., target values and/or constraints), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific EHR fields described above, but may be utilized to evaluate the quality of other fields in an EHR. For example, instead of observations, the present invention embodiments may be used to evaluate lab results.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method of managing electronic health records comprising:
    monitoring, via a processor, messages sent over a network between the processor and a client device;
    identifying within the monitored messages, via the processor, an update by a healthcare provider to an electronic health record of a patient;
    evaluating, via the processor, a quality of the identified update by a machine learning classifier built using vectors of natural language features extracted from a corpus of electronic health records; and
    in response to the identified update failing the evaluation:
        generating, via the processor, a survey including at least one inquiry;
        transmitting, via the processor, the survey with the at least one inquiry to each of the healthcare provider and the patient;
        comparing, via the processor, responses from the healthcare provider and the patient to same inquiries of the survey;
        notifying, via the processor, one or more selected from a group of the healthcare provider and the patient to perform an action in response to at least one difference between the responses from the healthcare provider and the patient; and
        modifying, via the processor, information within the electronic health record based on one or more responses to the at least one inquiry of the survey.

2. The method of claim 1, wherein evaluating a quality of the identified update comprises:
    determining a metric value indicating a quality of the identified update;
    comparing the metric value to a quality threshold; and
    determining whether the metric value satisfies the quality threshold.

3. The method of claim 1, wherein evaluating a quality of the identified update comprises:
    extracting one or more attributes of one or more free form text fields in the identified update; and
    comparing the one or more extracted attributes to one or more attributes of free form text fields of pre-determined quality.

4. The method of claim 1, wherein modifying information within the electronic health record comprises:
    augmenting the information of the electronic health record based on the one or more responses to the at least one inquiry of the survey.

5. The method of claim 1, wherein modifying information within the electronic health record further comprises:
    providing the one or more responses from the patient to the at least one inquiry of the survey for review.

6. The method of claim 1, wherein the identified update to the electronic health record includes unstructured data.

7. The method of claim 1, further comprising:
    generating the machine learning classifier to evaluate a quality of an update by training the machine learning classifier with information pertaining to entries for electronic health records produced by healthcare providers; and
    wherein evaluating a quality of the identified update further comprises applying the identified update to the machine learning classifier.

8. A system for managing electronic health records, comprising:
    at least one processor configured to:
        monitor messages sent over a network between the at least one processor and a client device;
        identify within the monitored messages an update by a healthcare provider to an electronic health record of a patient;
        evaluate a quality of the identified update by a machine learning classifier built using vectors of natural language features extracted from a corpus of electronic health records; and
        in response to the identified update failing the evaluation:
            generate a survey including at least one inquiry;
            transmit the survey with the at least one inquiry to each of the healthcare provider and the patient;
            compare responses from the healthcare provider and the patient to same inquiries of the survey;
            notify one or more selected from a group of the healthcare provider and the patient to perform an action in response to at least one difference between the responses from the healthcare provider and the patient; and
            modify information within the electronic health record based on one or more responses to the at least one inquiry of the survey.

9. The system of claim 8, wherein the at least one processor is configured to evaluate a quality of the identified update by:
- determining a metric value indicating a quality of the identified update;
- comparing the metric value to a quality threshold; and
- determining whether the metric value satisfies the quality threshold.

10. The system of claim 8, wherein the at least one processor is configured to evaluate a quality of the identified update by:
- extracting one or more attributes of one or more free form text fields in the identified update; and
- comparing the one or more extracted attributes to one or more attributes of free form text fields of pre-determined quality.

11. The system of claim 8, wherein the at least one processor is configured to modify information within the electronic health record by:
- augmenting the information of the electronic health record based on the one or more responses to the at least one inquiry of the survey.

12. The system of claim 8, wherein the at least one processor is configured to:
- generate the machine learning classifier to evaluate the quality of an update to an electronic health record by training the machine learning classifier with information pertaining to entries for electronic health records produced by healthcare providers; and
- evaluate the quality of the identified update by applying the identified update to the machine learning classifier.

13. A computer program product for managing electronic health records, the computer program product comprising a computer readable storage medium having program instructions embodied therewith, the program instructions executable by a computer processor to cause the computer processor to:
- monitor messages sent over a network between the computer processor and a client device;
- identify within the monitored messages an update by a healthcare provider to an electronic health record of a patient;
- evaluate a quality of the identified update by a machine learning classifier built using vectors of natural language features extracted from a corpus of electronic health records; and
- in response to the identified update failing the evaluation:
  - generate a survey including at least one inquiry;
  - transmit the survey with the at least one inquiry to each of the healthcare provider and the patient;
  - compare responses from the healthcare provider and the patient to same inquiries of the survey;
  - notify one or more selected from a group of the healthcare provider and the patient to perform an action in response to at least one difference between the responses from the healthcare provider and the patient; and
  - modify information within the electronic health record based on one or more responses to the at least one inquiry of the survey.

14. The computer program product of claim 13, wherein the program instructions are executable by the computer processor to cause the computer processor to evaluate a quality of the identified update by:
- determining a metric value indicating a quality of the identified update;
- comparing the metric value to a quality threshold; and
- determining whether the metric value satisfies the quality threshold.

15. The computer program product of claim 13, wherein the program instructions are executable by the computer processor to cause the computer processor to evaluate a quality of the identified update by:
- extracting one or more attributes of one or more free form text fields in the identified update; and
- comparing the one or more extracted attributes to one or more attributes of free form text fields of pre-determined quality.

16. The computer program product of claim 13, wherein the program instructions are executable by the computer processor to cause the computer processor to:
- modify information within the electronic health record by:
  - augmenting the information of the electronic health record based on the one or more responses to the at least one inquiry of the survey.

17. The computer program product of claim 13, wherein the program instructions are executable by the computer processor to cause the computer processor to:
- generate the machine learning classifier to evaluate a quality of an update to an electronic health record by training the machine learning classifier with information pertaining to entries for electronic health records produced by healthcare providers; and
- evaluate the quality of the identified update by applying the identified update to the machine learning classifier.

* * * * *